(12) United States Patent
Babak et al.

(10) Patent No.: US 11,207,114 B2
(45) Date of Patent: Dec. 28, 2021

(54) PIN PLACEMENT HOLDER FOR SURGICAL PIN DRIVER

(71) Applicant: THINK SURGICAL, INC., Fremont, CA (US)

(72) Inventors: Kianmajd Babak, Fremont, CA (US); Joel Zuhars, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 3 days.

(21) Appl. No.: 16/336,370

(22) PCT Filed: Sep. 25, 2017

(86) PCT No.: PCT/US2017/053252
§ 371 (c)(1),
(2) Date: Mar. 25, 2019

(87) PCT Pub. No.: WO2018/058036
PCT Pub. Date: Mar. 29, 2018

(65) Prior Publication Data
US 2019/0216520 A1     Jul. 18, 2019

Related U.S. Application Data

(60) Provisional application No. 62/399,634, filed on Sep. 26, 2016.

(51) Int. Cl.
*A61B 17/88* (2006.01)
*A61B 17/16* (2006.01)
(Continued)

(52) U.S. Cl.
CPC ........ *A61B 17/8897* (2013.01); *A61B 17/162* (2013.01); *A61B 17/1624* (2013.01);
(Continued)

(58) Field of Classification Search
CPC ............ A61B 17/8897; A61B 2017/90; A61B 17/162; A61B 17/1624; A61B 17/1633;
(Continued)

(56) References Cited

U.S. PATENT DOCUMENTS

| 5,514,145 A | * | 5/1996 | Durham ............. A61B 17/1707 408/115 R |
| 5,793,346 A | | 8/1998 | Moon |

(Continued)

FOREIGN PATENT DOCUMENTS

| JP | 3187722 B2 | 7/2001 |
| JP | 2005279270 A | 10/2005 |

(Continued)

OTHER PUBLICATIONS

International Search Report dated Jan. 10, 2018.
(Continued)

*Primary Examiner* — Kevin T Truong
*Assistant Examiner* — Lisa Nguyen
(74) *Attorney, Agent, or Firm* — Blue Filament Law PLLC (57) ABSTRACT

A surgical device for pin insertion in a bone of a subject to aid in performing a bone cutting procedure is provided that includes a drive portion configured to drive a pin for insertion into the bone. The drive portion has a pin drive assembly with a shaft Q having a shaft proximal end. At least one magnet is associated with the shaft proximal end adapted for attraction and retention of the pin in the shaft proximal end. A spindle assembly is adapted to drive the shaft so as to rotate the pin into the bone to a degree of bone retention that overcomes the attraction and the retention of the pin in the shaft proximal end. An alignment system for
(Continued)

surgical bone cutting procedures inclusive of the same is also provided along with a method for aligning a cutting guide on a subject's bone.

15 Claims, 7 Drawing Sheets (51) Int. Cl.
| | |
|---|---|
| *A61B 34/20* | (2016.01) |
| *A61B 17/17* | (2006.01) |
| *A61F 2/46* | (2006.01) |
| *A61B 17/84* | (2006.01) |
| *A61B 17/56* | (2006.01) |
| *A61B 90/00* | (2016.01) |
| *A61F 2/30* | (2006.01) |

(52) U.S. Cl.
CPC ...... *A61B 17/1697* (2013.01); *A61B 17/1764* (2013.01); *A61B 34/20* (2016.02); *A61B 90/00* (2016.02); *A61F 2/461* (2013.01); *A61B 17/848* (2013.01); *A61B 2017/564* (2013.01); *A61B 2090/3983* (2016.02); *A61F 2002/3069* (2013.01)

(58) Field of Classification Search
CPC . A61B 17/17; A61B 17/1717; A61B 17/1721; A61B 17/1725; A61B 17/1753; A61B 17/92; A61B 17/8875; A61B 17/7082
USPC .......................................... 606/104; 600/426
See application file for complete search history.

(56) References Cited

U.S. PATENT DOCUMENTS

| | | | | |
|---|---|---|---|---|
| 5,800,440 | A * | 9/1998 | Stead ................. | A61B 17/1697 606/104 |
| 7,803,158 | B2 | 9/2010 | Hayden | |
| 8,737,700 | B2 | 5/2014 | Park et al. | |
| 8,977,021 | B2 | 3/2015 | Kang et al. | |
| 9,855,069 | B2 * | 1/2018 | Jezierski .......... | A61B 17/32002 |
| 2005/0216032 | A1 * | 9/2005 | Hayden .................. | A61B 17/17 606/130 |
| 2007/0270680 | A1 | 11/2007 | Sheffer et al. | |
| 2012/0253411 | A1 | 10/2012 | Lozier et al. | |
| 2013/0060278 | A1 * | 3/2013 | Bozung ................. | A61F 2/4611 606/205 |
| 2013/0144570 | A1 * | 6/2013 | Axelson, Jr. .......... | A61B 34/10 703/1 |
| 2013/0261609 | A1 | 10/2013 | DiCorleto et al. | |
| 2013/0274769 | A1 * | 10/2013 | Bonutti .............. | A61B 17/0483 606/148 |
| 2014/0324059 | A1 * | 10/2014 | Stemniski .......... | A61B 17/1717 606/96 |
| 2015/0238206 | A1 * | 8/2015 | Benson .................. | A61B 17/17 606/86 A |
| 2015/0273208 | A1 | 10/2015 | Hamilton | |
| 2016/0242792 | A1 | 8/2016 | Sasing et al. | |
| 2017/0156799 | A1 | 6/2017 | Bozung | |
| 2018/0000526 | A1 * | 1/2018 | O'Neil .................. | A61B 90/39 |

FOREIGN PATENT DOCUMENTS

| | | |
|---|---|---|
| JP | 2015502180 A | 1/2015 |
| WO | 2005087125 A2 | 9/2005 |
| WO | 2007017642 A1 | 2/2007 |
| WO | 2015056053 A1 | 4/2015 |
| WO | 2016080921 A1 | 5/2016 |

OTHER PUBLICATIONS

Supplementary Partial European Search Report dated Feb. 26, 2020, issued in corresponding European Appln. No. EP17760777.
Supplementary Partial European Search Report dated Jun. 25, 2020, issued in corresponding European Appln. No. EP17854072.
Notice of Reasons for Rejection for JP2019-507096, dated May 31, 2021.

* cited by examiner

PIN PLACEMENT HOLDER FOR SURGICAL PIN DRIVER

RELATED APPLICATIONS

This application claims priority benefit of U.S. Provisional Application Ser. No. 62/399,634 filed 26 Sep. 2016; the contents of which are hereby incorporated by reference.

TECHNICAL FIELD

The present invention generally relates to computer assisted surgery, and more specifically to an improved pin placement holder for tools used for actively aligning pins in orthopedic surgical applications.

BACKGROUND

Total knee arthroplasty (TKA) is a surgical procedure in which the articulating surfaces of the knee joint are replaced with prosthetic components, or implants. TKA requires the removal of worn or damaged articular cartilage and bone on the distal femur and proximal tibia. The removed cartilage and bone is then replaced with synthetic implants, typically formed of metal or plastic, to create new joint surfaces.

The position and orientation (POSE) of the removed bone, referred to as bone cuts or resected bone, determines the final placement of the implants within the joint. Generally, surgeons plan and create the bone cuts so the final placement of the implants restores the mechanical axis or kinematics of the patient's leg while preserving the balance of the surrounding knee ligaments. Even small implant alignment errors outside of clinically acceptable ranges correlate to significantly worse outcomes and increased rates of revision surgery. In TKA, creating the bone cuts to correctly align the implants is especially difficult because the femur requires at least five planar bone cuts to receive the femoral prosthesis. The planar cuts must be aligned in at least five degrees of freedom to ensure a proper orientation: anterior-posterior translation, proximal-distal translation, external-internal rotation, varus-valgus rotation, and flexion-extension rotation. Any misalignment in any one of the planar cuts or orientations may have drastic consequences on the final result of the procedure and the wear pattern of the implant.

Cutting guides, also referred to as cutting blocks or cutting jigs, are commonly used to aid in creating the bone cuts. The cutting guides include guide slots to restrict or align a bone removal device, such as an oscillating saw, in the correct bone resection plane. Cutting guides are advantageous for several reasons. For one, the guide slots stabilize the bone removal device during cutting to ensure the bone removal device does not deflect from the desired plane. Additionally, a single cutting guide may contain multiple guide slots to accurately align and resect two or more cutting places, such as a 4-in-1 cutting block. Finally, the guide slots and the working end of the oscillating saw are typically planar in shape, which make them ideal for creating planar bone cuts. The advantages of using a cutting guide are apparent, however, the cutting guide still needs to be accurately positioned on to the bone prior to executing the cut. In fact, it is the placement of the guide slots on the bone that remains one of the most difficult, tedious and critical tasks for surgeons during TKA.

Figure 1A:
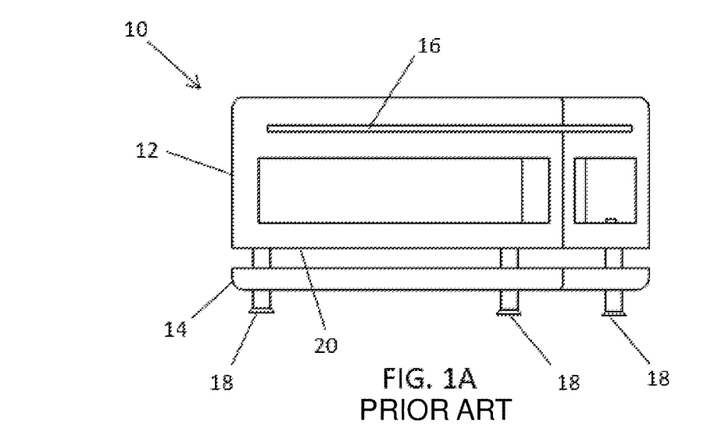
FIGS. 1A and 1B illustrate perspective views of a distal cutting guide.
Figure 1B:
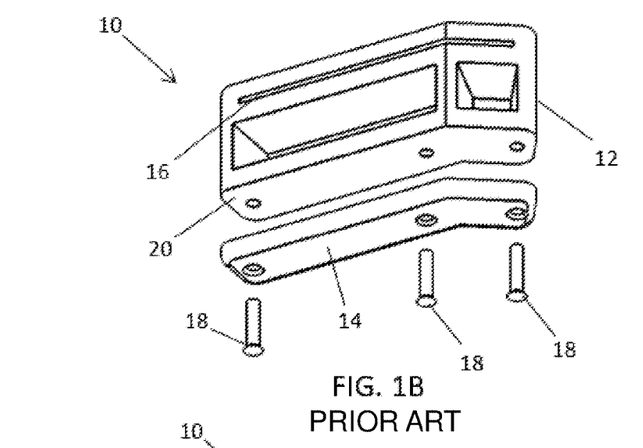
Figure 1C:
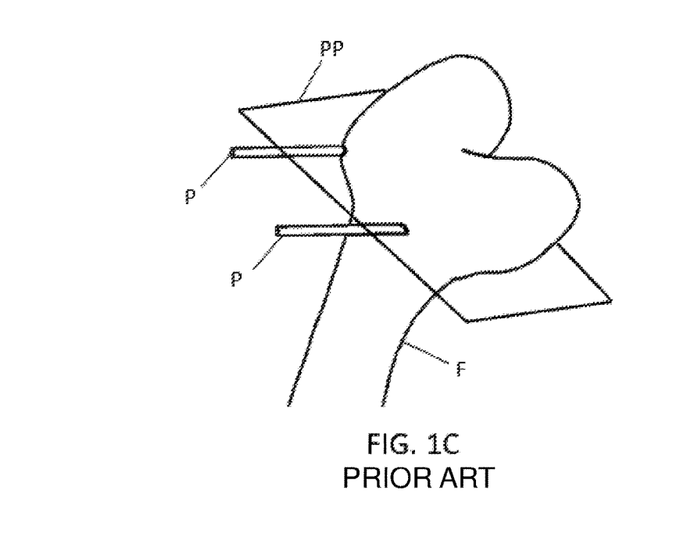
FIG. 1C illustrates a set of pins driven coincident with a virtual pin plane in a femoral bone.
Figure 1D:
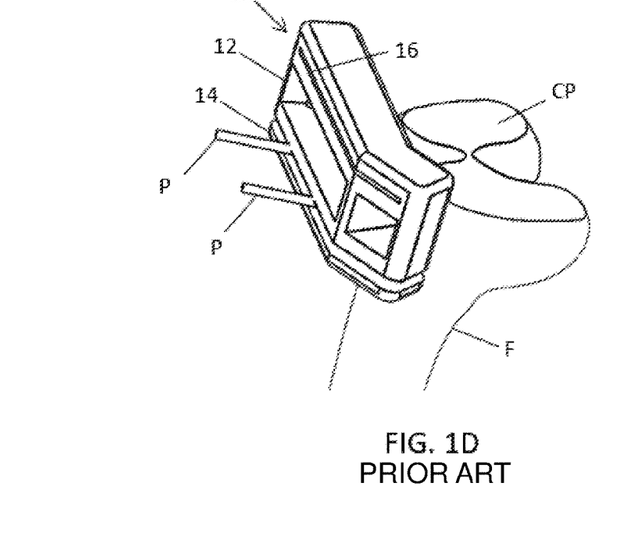
FIG. 1D illustrates the distal cutting guide of FIGS. 1A and 1B assembled to the pins of FIG. 1C.

FIGS. 1A and 1B illustrate perspective views of a distal cutting guide 10 disclosed in U.S. Prov. App. No. 62/259,487 assigned to the assignee of the present application and incorporated by reference herein in its entirety. FIG. 1A is a front elevation view of the distal cutting guide 10 and FIG. 1B is a perspective view thereof. In general, cutting guides 10 and alignment guides used herein are made of a rigid or semi-rigid material, such as stainless steel, aluminum, titanium, polyetheretherketone (PEEK), polyphenylsulfone, acrylonitrile butadiene styrene (ABS), and the like. The distal cutting guide 10 includes a guide portion 12 and an attachment portion 14. The guide portion 12 includes a guide slot 16 and a bottom surface 20. The guide slot 16 is for guiding a surgical saw in creating the planned distal cut CP (see FIG. 1D) on the femur F. The bottom surface 20 may abut against one or more bone pins P that are placed on the femur F as shown in FIG. 1C. The attachment portion 14 and the guide portion 12 clamp to the bone pins P using fasteners 18. Here, the virtual pin plane PP for the distal cut guide 10 is defined in a surgical plan by planning software using the POSE of the planned distal cut plane CP (shown in FIG. 1D), and the distance between the guide slot 16 and the bottom surface 20 of the guide portion 12. The planning software may also use the known width of the bone pins P. For example, the pin plane PP may be defined by proximally translating the planned distal cut plane CP by the distance between the guide slot 16 and the bottom surface 20 of the distal cutting guide 10. The software may further proximally translate the planned distal cut plane CP by an additional half width of the pins P. Therefore, when the cutting guide 10 is clamped to the bone pins P as shown in FIG. 1D, the guide slot 16 is aligned with the planned distal cut plane CP.

U.S. Provisional Patent application 62/259,487 also describes a system and method for aligning a cutting guide on the bone. The system utilizes a dynamic two degree-of-freedom (DOF) hand-held articulating device and a patient specific surgical plan to accurately align one or more pins on to the bone. A cutting guide with one or more guide slots is assembled to the pins where the final POSE of the guide slot(s) correspond with the POSE of the desired bone cuts. Although the 2-DOF hand-held system may accurately align the pins, one design challenge was determining how to removably secure the pin to the articulating device and maintain the rotational concentricity of the pin during operation. A simple approach was to use a standard 3 jaw chuck, or a collet system to hold and secure the pin to the driving tool. The problem with the 3-jaw chuck or collet for securing a pin is that they require the use of both hands of the surgeon or involvement of a surgical assistant. One hand to insert the pin, and the second hand to close the chuck or the collet. This process that relies on use of both hands by the surgeon or involvement of an assistant may be a source of distraction and, is prone to the introduction of errors in the pin alignment, and surgeon fatigue.

Thus, there is a need for a system and method to accurately align and insert one or more pins in the bone using a pin driving device that does not require both of the surgeon or operator's hands to load a pin into the device and release the pin from the device once the pin is inserted in the bone. There is a further need for a mechanism and pin holder design that maintains the rotational concentricity of the pin while operating the device.

SUMMARY OF THE INVENTION

A surgical device for pin insertion in a bone of a subject to aid in performing a bone cutting procedure is provided that includes a drive portion configured to drive a pin for insertion into the bone. The drive portion has a pin drive assembly with a shaft having a shaft proximal end. At least one magnet is associated with the shaft proximal end adapted for attraction and retention of the pin in the shaft proximal end. A spindle assembly is adapted to drive the shaft so as to rotate the pin into the bone to a degree of bone retention that overcomes the attraction and the retention of the pin in the shaft proximal end.

An alignment system for surgical bone cutting procedures includes a plurality of bone pins inserted with the surgical device within a virtual plane relative to a cut plane to be created on a subject's bone. A tracking system tracks the position and orientation (POSE) of the working portion of the surgical device. A cutting guide is configured to be received on to the plurality of bone pins, with one or more guide slots within the cutting guide being present and configured to guide a surgical saw to make surgical cuts on the subject's bone. A computing system is part of the alignment system and programmed to:

define the virtual plane relative to the cut plane to be created on the subject's bone;

determine a relationship between a location of the working portion of the surgical device and the virtual plane; and supply a series of commands to the set of components in the hand-held portion to control pitch and translation to maintain the pin insertion axis with the virtual plane.

A method for aligning a cutting guide on a subject's bone is also provided in which one or more cut planes from a surgical plan obtained with planning software is determined. One or more virtual planes relative to each of the one or more cut planes to be created on the subject's bone is also then determined. The aforementioned surgical device is used for aligning and inserting a plurality of bone pins within a virtual plane from the one or more virtual planes. A cutting guide is attached that is configured to clamp on to the plurality of inserted bone pins and has one or more guides slots configured to guide a surgical saw to make surgical cuts on the subject bone that correspond to the one or more cut planes.

BRIEF DESCRIPTION OF THE DRAWINGS

The present invention is further detailed with respect to the following drawings that are intended to show certain aspects of the present of invention, but should not be construed as limit on the practice of the invention, wherein.

DETAILED DESCRIPTION

The present invention has utility as a system and method to aid a surgeon in quickly and precisely aligning a guide pin on a bone of a subject, with the aid of a pin placement holder in a pin driver assembly. In contrast to other prior art mechanisms, the present invention does not require an operator to use two hands to load and secure a pin. Certain embodiments of the inventive pin driver assembly use a pin guide that aligns an inserted pin to a shaft, where the shaft has a hex socket to rotationally lock the pin to the rotation of the shaft. The shaft also houses two small magnets to attract and secure the inserted pin, the magnets taking the place of a conventional 3-jaw chuck, or a collet system to hold and secure the pin to the driving tool, and thereby eliminate the need for the operator to use both of their hands to secure the pin to the driving tool or rely on a second person to assist. The magnets pull the inserted pin into the hex socket and prevents the pin from falling out of the pin guide or the hex socket, the magnet or magnets have a limited Gauss strength balance to retain the pin prior to bone securement, yet release the pin upon securement. The operator or surgeon can freely articulate the tool in any angle without worry of the pin falling out of the device.

The system and method is especially advantageous for total knee arthroplasty and revision knee arthroplasty where the position and orientation (POSE) of the pins are used to assemble and align a cutting guide thereon to facilitate the creation of a desired cut plane. However, it should be appreciated that other medical applications may exploit the subject matter disclosed herein such as osteotomies and high tibial osteotomies, and the placement of screws for spinal fusions and spinal reconstruction, maxillofacial surgery, fractures, and other procedures requiring the precise placement of bone pins, screws, or nails. Similarly, embodiments of the invention described herein may be adapted for use in a non-medical setting wherever the precise placement of a screw, nail, or rivet is needed such as construction, aircraft assembly and carpentry with the proviso that at least a portion of the fasteners are ferromagnetic.

The following description of various embodiments of the invention is not intended to limit the invention to these specific embodiments, but rather to enable any person skilled in the art to make and use this invention through exemplary aspects thereof. As used herein, a patient, or synonymously a subject, is defined as a human, a non-human primate; or an animal of a horse, a cow, a sheep, a goat, a cat, a rodent and a bird; or a cadaver of any of the aforementioned.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

Figure 2:
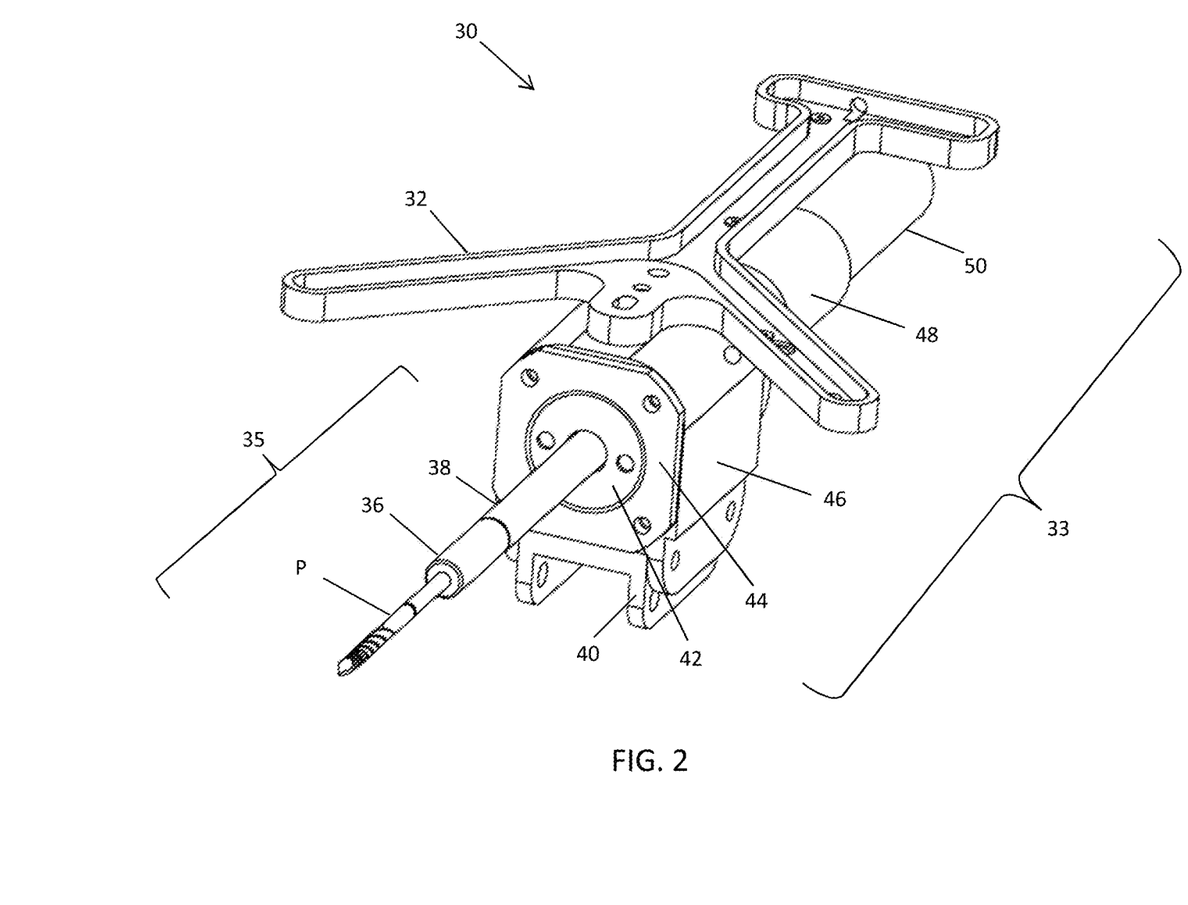
FIG. 2 is a perspective view of a drive portion of a hand-held end effector in accordance with embodiments of the invention.
Figure 3:
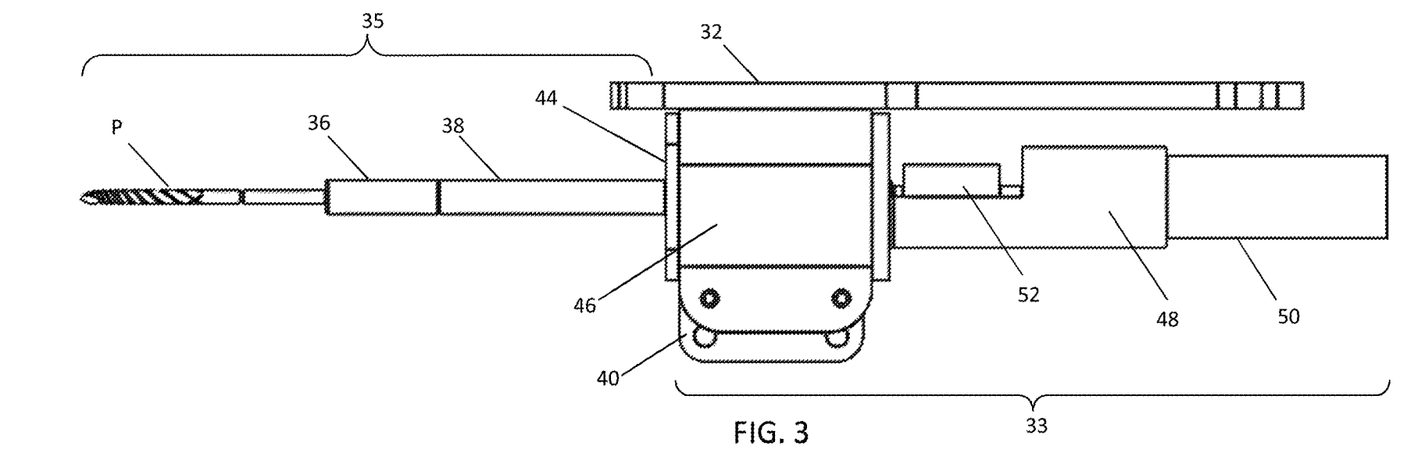
FIG. 3 is a side view of the drive portion of a hand-held end effector shown in FIG. 2 in accordance with embodiments of the invention.
Figure 4:
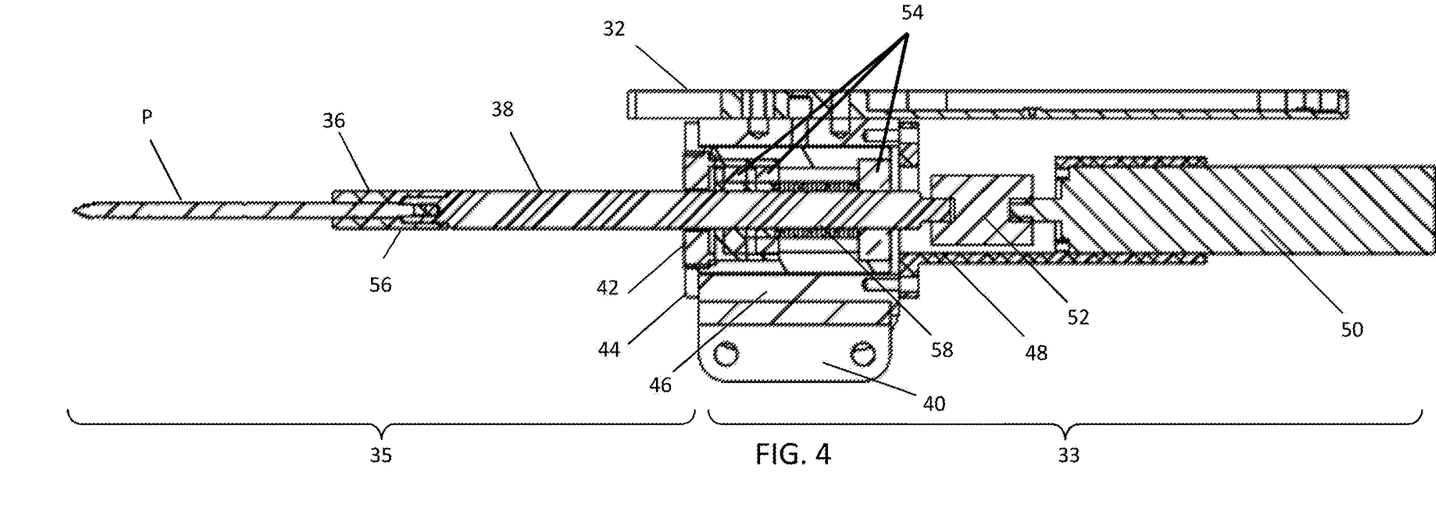
FIG. 4 is a central longitudinal cross-sectional view of FIG. 3 in accordance with embodiments of the invention.
Figure 5A:
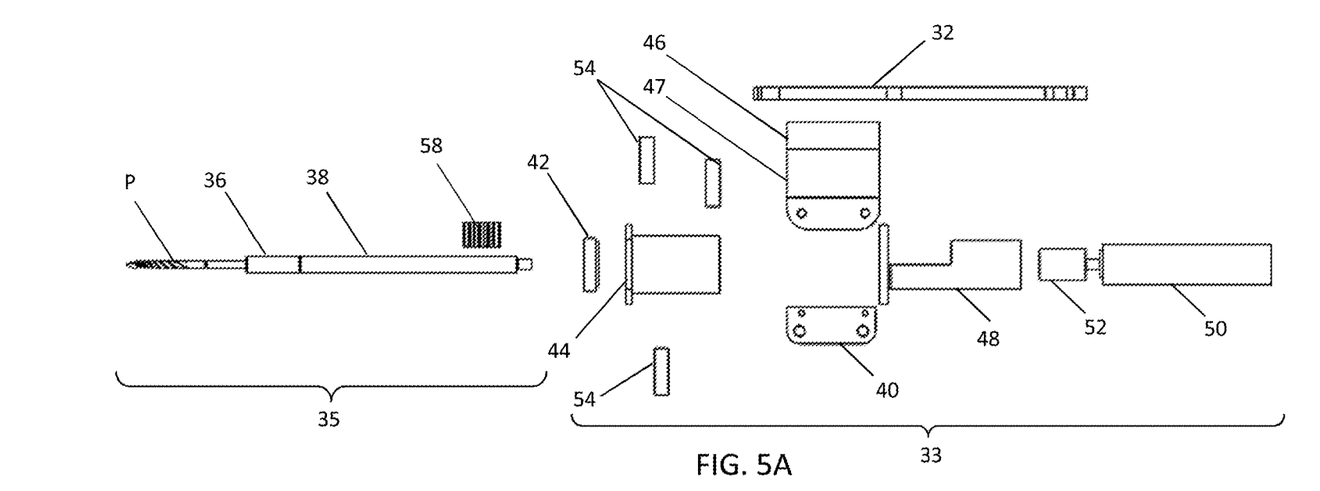
FIG. 5A is an exploded view of FIG. 3 in accordance with embodiments of the invention.
Figure 5B:
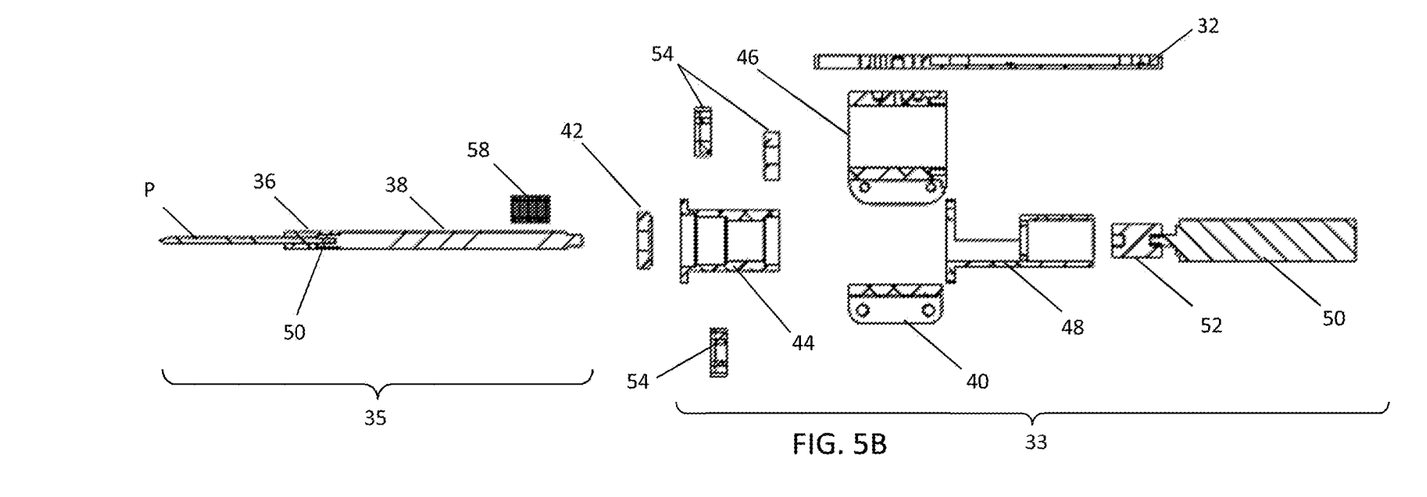
FIG. 5B is an exploded view of FIG. 4 in accordance with embodiments of the invention.
Figure 6:
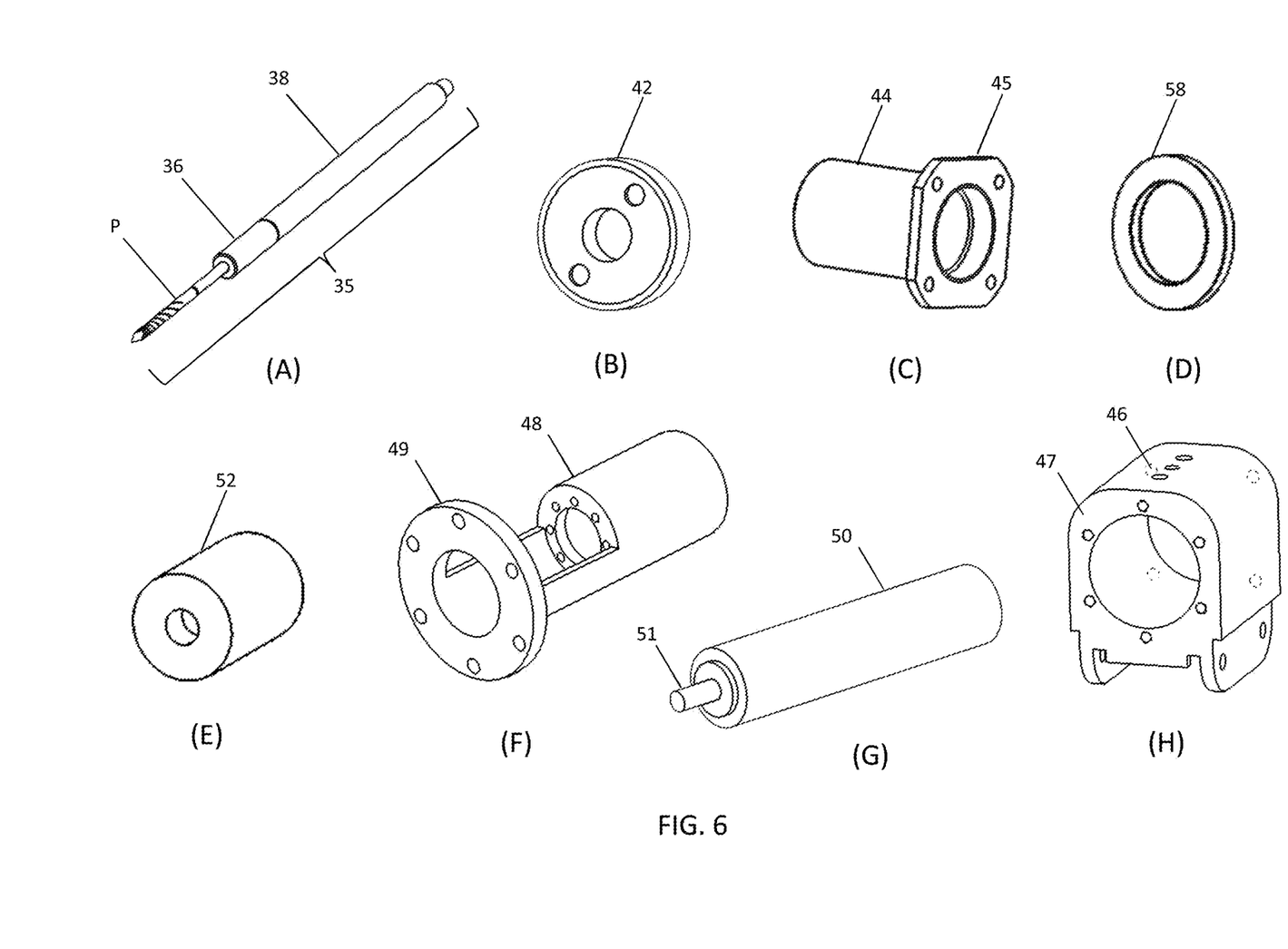
FIGS. 6A-6H are detailed individual perspective views of the major components that form the drive portion of a hand-held end effector in accordance with embodiments of the invention.
Figure 7A:
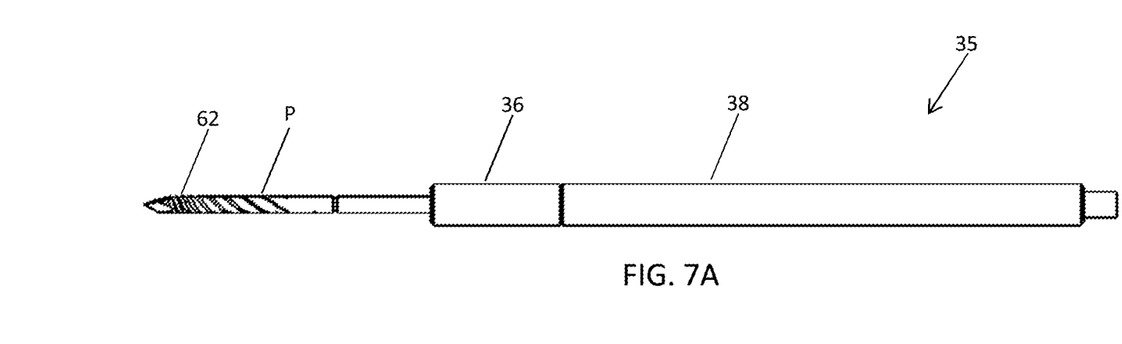
FIG. 7A is a detailed side view of the pin drive assembly in accordance with embodiments of the invention.
Figure 7B:
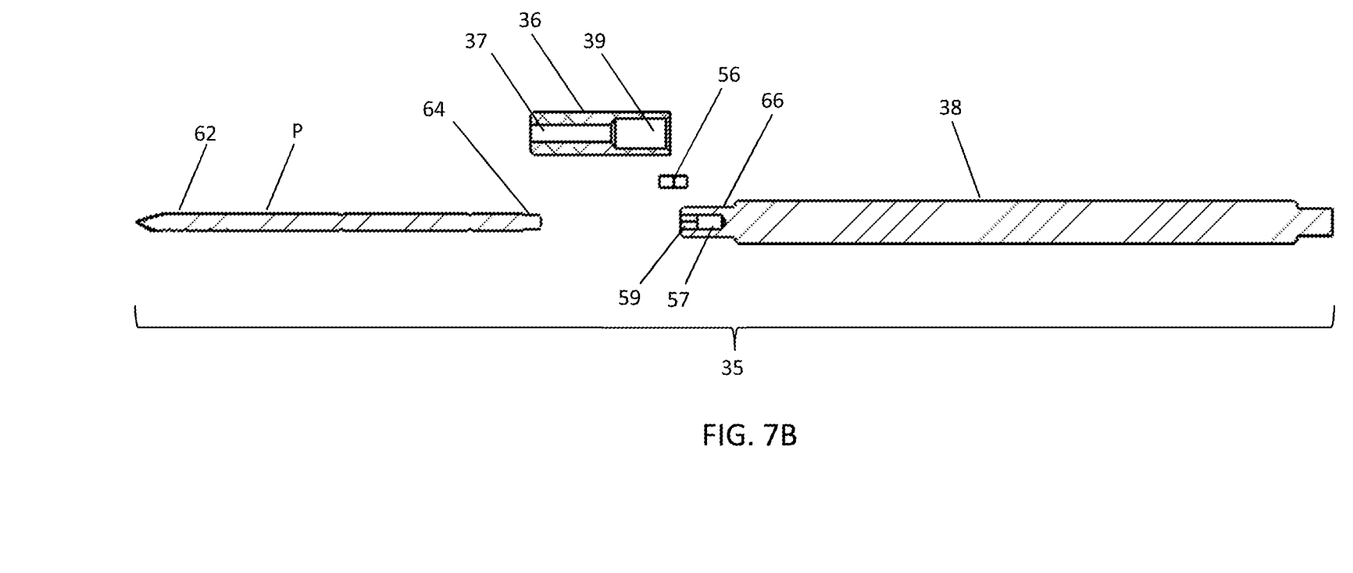
FIG. 7B is a detailed exploded and central longitudinal cross-sectional side view of the pin drive assembly in accordance with embodiments of the invention.
Figure 8:
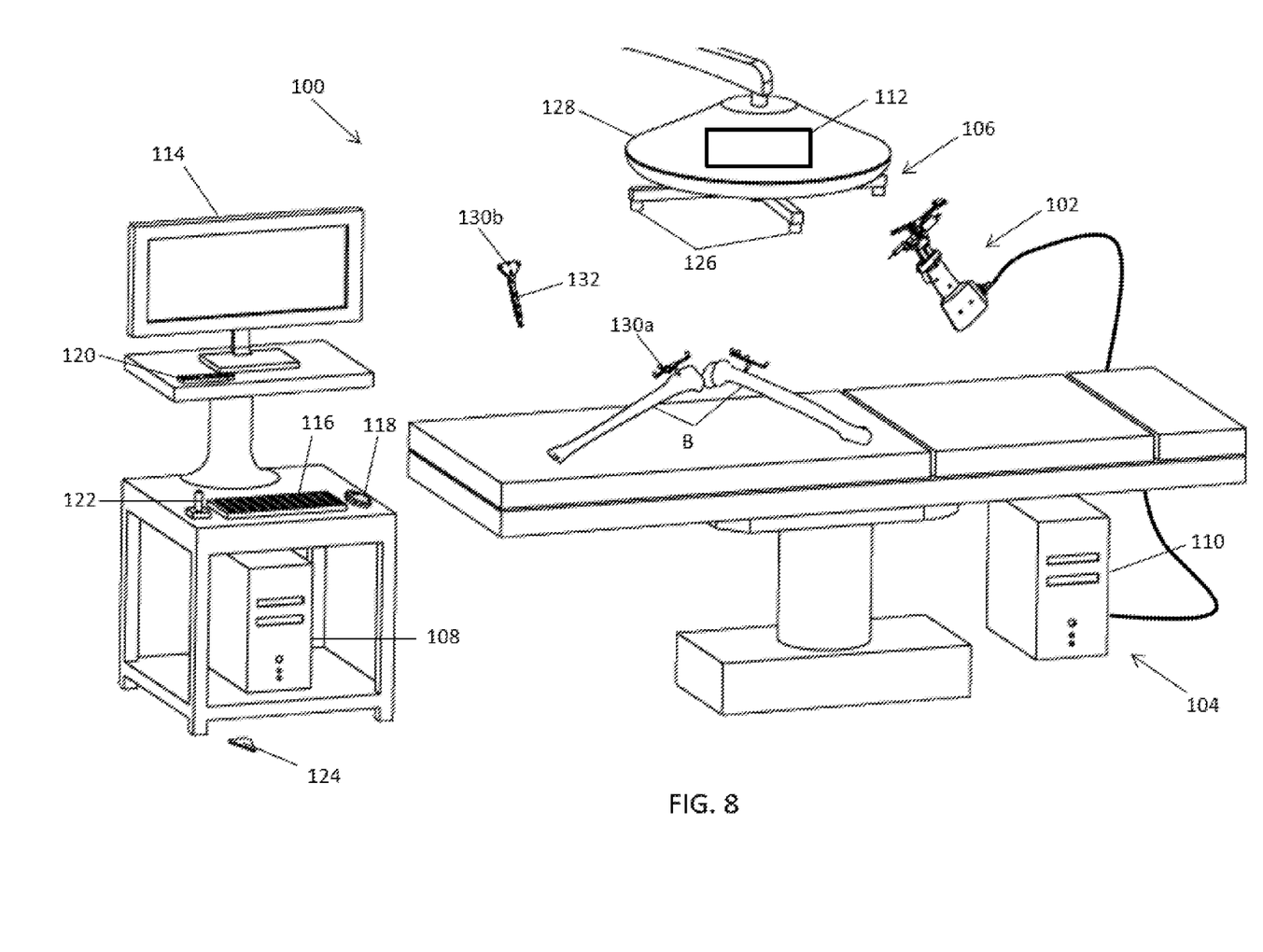
FIG. 8 illustrates a surgical system in the context of an operating room (OR) in accordance with embodiments of the invention.

Referring now to the figures, FIG. 2 is a perspective view of an inventive drive portion 30 of a hand held surgical device 102, also referred to herein as a pin-driver device (see FIG. 8). FIG. 3 is a side view of the drive portion 30, while FIG. 4 is a central plane, longitudinal cross-sectional view of FIG. 3. FIG. 5A is an exploded view of FIG. 3, and FIG. 5B is an exploded view of FIG. 4. FIGS. 6A-6H are detailed individual perspective views of the major components that form the drive portion 30. FIG. 7A is a detailed side view of the pin drive assembly 35, and FIG. 7B is a detailed exploded and central longitudinal cross-sectional side view of the pin drive assembly 35. It is noted that embodiments of the inventive pin drive assembly 35 may also be used with end effectors for robots as well as hand held devices. The drive portion 30 has two major subassemblies a spindle assembly 33 and a pin drive assembly 35. The modular design of the spindle assembly 33 allows for the changing and integration of several different parts. The spindle assembly 33 has the following major subcomponents: a bearing cap 42, a bearing holder 44, a set of disk springs 58, a coupler 52, a motor holder 48, a motor 50, and a spindle cartridge 46. The bearing cap 42 squeezes the outer cage of the bearing to facilitate preloading on angular contact bearings. The bearing holder 44 holds an arrangement of bearings 54, and provides a modular connection to the spindle cartridge 46. The flange 45 is perpendicular to the bearing axis to guarantee perpendicularity to the spindle cartridge 46. It is appreciated that the major subcomponents of the spindle assembly 33 may be exchanged with minimal effects or changes to the other parts. For example, the motor holder 48 is readily changed to accommodate many different size motors and still be capable of attachment to the spindle cartridge 46. The set of disk springs 58 reduce the impact and vibration forces between the bearings 54. The coupler 52 attaches a pin drive shaft 38 of the pin drive assembly to the motor shaft 51. The motor holder 48 holds the motor 50, provides room for the coupler 52, and has a flange 49 connection that attaches to the spindle cartridge 46. The flat side of the flange 49 guarantees that the motor axis is perpendicular to the spindle cartridge wall 47. In addition, the flange 49 has allowance to translationally move the motor axis shaft to decrease radial misalignment between the pin drive shaft 38 and the motor shaft 51.

The spindle cartridge 46 serves as the centerpiece of the spindle assembly 33. The spindle cartridge 46 has two parallel flange walls 47 to attach the bearing holder 44, and the motor holder 48 to facilitate a corridor or parallel shafts between the motor 50 and the pin drive assembly 35. The spindle cartridge 46 may also have a mechanism, such as a screw, clasp, or other fastener, to permit a fiducial marker array 32 to attach to the drive portion 30. In other embodiments, the fiducial marker array 32 or individual fiducial markers are an integral part of the drive portion 30. A hand-held attachment member 40 connects with the spindle cartridge 46 and is adapted to pivotally attach with the hand-held portion of the hand-held surgical device 102. The fiducial markers may be active markers such as light emitting diodes (LEDs), passive markers such as retroreflective spheres, or other tracking reference markers such as magnetic sensors, ultrasonic beacons, inertial measuring units, and combinations thereof.

The pin drive assembly 35 is designed to increase surgical usability and accuracy. The pin drive assembly 35 has the following major subcomponents: a pin drive shaft 38, a pin guide 36, and a magnet 56. The pin drive assembly 35 assembles to the spindle assembly 33 by way of the pin drive shaft 38, where the pin drive shaft 38 runs through the spindle cartridge 46 via the bearing holder 44, and attaches to the motor 50 via the coupler 52. In operation, a surgeon places a pin P into the pin guide 36. At least one magnet 56, which is fixed in the pin drive shaft 38, snap a male hex end 64 of the pin P into a hex socket 59 of the pin drive shaft 38. In a specific embodiment of the present invention, the magnets 56 are adhesively bonded to the pin drive shaft 38 in a magnet holder 57 that is proximal to the hex socket 59. The magnet(s) 56 prevent the pin P from falling out of the pin guide 36 by keeping a magnetic attractive force on the magnetically attracted metallic pin P. The pin guide 36 has a distal end 37 and a proximal end 39. The inner diameter of the distal end 37 is tightly dimensioned to the outer diameter of the pin P, and fits over the pin P with a small amount of clearance that constrains the pin's rotational axis to the shaft's rotational axis with a very little amount of play. The pin guide proximal end 39 has an inner diameter larger than that of the distal end 37 and is tightly dimensioned to the outer diameter of a distal portion 66 of the pin drive shaft 38. The design of the pin guide 36 stabilizes the pin P and makes the pin P rotate concentrically about the longitudinal axis of the shaft as the motor 50 drives (i.e. rotates) the pin P. One may accomplish this stabilization and alignment by manufacturing the pin drive shaft 38 with a deeper hex socket; however, there are manufacturing constraints and added costs to do so. Therefore, the pin guide 36 is advantageous from a manufacturing point of view.

The hex socket 59 on the pin drive shaft 38 rotates the pin P, which causes the pin P to drill deep inside a subject bone, and the grooves 62 on the pin P firmly hold the pin P in place. Once the pin P is firmly placed inside the subject bone, the magnetic pull force on the pin P is overcome and the pin P releases from the pin driver assembly 35 as the surgeon removes the pin driver assembly 35. In a specific inventive embodiment, the pin P is made of magnetically attractive stainless steel and the pin guide 36 is made of aluminum.

FIG. 8 illustrates an inventive embodiment of a pin driving surgical system 100 in the context of an operating room (OR). The surgical system 100 generally includes an articulating surgical device 102 with embodiments of the drive portion 30, a computing system 104, and a tracking system 106. The surgical system 100 is able to guide and assist a user in accurately placing pins coincident with a virtual plane that is defined relative to a subject's bone. The virtual plane is defined in a surgical plan such that a cutting guide when assembled to the inserted pins align one or more guide slots with the bone cuts required to receive a prosthetic implant in a planned position and orientation.

Computing System and Tracking System

The pin-driver device 102 is controlled by commands from the computing system 104 to maintain the coincidence of the longitudinal axis of the pin P with a virtual plane defined in the surgical plan. The computing system 104 may include a planning computer 108 including a processor; a device computer 110 including a processor; a tracking computer 112 including a processor; and peripheral devices. Processors operate in the computing system 104 to perform computations associated with the inventive system and method. It is appreciated that processor functions are shared between computers, a remote server, a cloud computing facility, or combinations thereof.

In a particular embodiment, the device computer 110 may include one or more processors, controllers, and any additional data storage medium such as RAM, ROM or other non-volatile memory to perform functions related to the operation of the surgical device 102. For example, the device computer 110 may include software, data, and utilities to control the surgical device 102, receive and process tracking data, execute registration algorithms, execute calibration routines, provide workflow instructions to the user throughout a surgical procedure, as well as any other suitable software, data or utilities required to successfully perform the procedure in accordance with embodiments of the invention.

The planning computer 108, device computer 110, and tracking computer 112 may be separate entities as shown, or it is contemplated that their operations may be executed on just one or two computers depending on the configuration of the surgical system 100. For example, the tracking computer 112 may have the operational data to control the device 102 without the need for a device computer 110. Or, the device computer 110 may include operational data to plan the surgical procedure without the need for the planning computer 108. In any case, the peripheral devices allow a user to interface with the surgical system 100 and may include: one or more user-interfaces, such as a display or monitor 114; and user-input mechanisms, such as a keyboard 116, mouse 118, pendent 120, joystick 122, foot pedal 124, or the monitor 114 may have touchscreen capabilities.

The planning computer 108 contains hardware (e.g., processors, controllers, and memory), software, data and utilities that are dedicated to aid a user in planning a surgical procedure, either pre-operatively or intra-operatively. This may include reading medical imaging data, segmenting imaging data, constructing and manipulating three-dimensional (3D) virtual models, storing and providing computer-aided design (CAD) files, planning the POSE of implants relative to the bone, defining virtual pin planes, and generating the surgical plan data for use with the system 100. The final surgical plan data may include an image data set of the bone, bone registration data points, subject identification information, the POSE of the implants relative to the bone, the POSE of one or more virtual planes defined relative to the bone, and any tissue modification instructions. The final surgical plan is readily transferred to the device computer 110 and/or tracking computer 112 through a wired or wireless connection in the operating room (OR); or transferred via a non-transient data storage medium (e.g., a compact disc (CD), a portable universal serial bus (USB) drive) if the planning computer 108 is located outside the OR.

The device computer 110 contains hardware, software, data and utilities that are primarily dedicated to the operation of the articulating device 102. This may include controlling the position and/or orientation (POSE) of the pin P, controlling the speed of the motor 50, the processing of kinematic and inverse kinematic data of the device 102, the execution of registration algorithms, the execution of calibration routines, the execution of surgical plan data, coordinate transformation processing, providing workflow instructions to the user, and utilizing POSE data from the tracking system 106.

The tracking system 106 includes two or more optical receivers 126 to detect the position of fiducial markers. A set of fiducial markers uniquely arranged on a rigid body is referred to herein as a fiducial marker array (32, 130a, 130b). Illustrative examples of the fiducial markers may include: an active transmitter, such as an LED or electromagnetic emitter; a passive reflector, such as a plastic sphere with a retro-reflective film; a distinct pattern or sequence of shapes, lines or other characters. An example of an optical tracking system is described in U.S. Pat. No. 6,061,644. The tracking system 106 may be built into a surgical light 128, located on a boom, a stand, or built into the walls or ceilings of the OR. The tracking system computer 112 may include tracking hardware, software, data and utilities to determine the POSE of objects (e.g., bones B, the articulating device 102) in a local or global coordinate frame. The POSE of the objects is also referred to herein as POSE data, where this POSE data is readily communicated to the device computer 110 through a wired or wireless connection. Alternatively, the device computer 110 may determine the POSE data using the position of the fiducial markers detected directly from the optical receivers 126.

The POSE data is determined using the position of the fiducial markers (130a, 130b, 130c) detected from the optical receivers 126 and operations/processes such as image processing, image filtering, triangulation algorithms, geometric relationship processing, registration algorithms, calibration algorithms, and coordinate transformation processing. POSE data from the tracking system 106 is used by the computing system 104 to perform various functions. For example, the POSE of a digitizer probe 132 with an attached probe fiducial marker array 130b may be calibrated such that the probe tip is continuously known as described in U.S. Pat. No. 7,043,961. The POSE of the tip or axis of the pin P may be known with respect to a device fiducial marker array 32 using a calibration method as described in U.S. Prov. Pat. App. 62/128,857. Registration algorithms are readily executed to determine the POSE and/or coordinate transforms between a bone B and the surgical plan, using the registration methods described in U.S. Pat. Nos. 6,033,415, and 8,287,522. For example, in a registration method, points on a patient bone may be collected from a tracked digitizer probe 132 to transform the coordinates of a surgical plan to the coordinates of the bone.

It should be appreciated that in certain embodiments, other tracking systems may be incorporated with the surgical system 100 such as an electromagnetic field tracking system, a mechanical tracking system or other tracking systems that utilize acoustic emitters or reflectors; magnetic emitters or reflectors; accelerometers; gyroscopes; and the like or any combinations thereof. In particular inventive embodiments, mechanical tracking systems may be used. The replacement of a non-mechanical tracking system with a mechanical tracking system should be apparent to one skilled in the art. In specific embodiments, the use of a mechanical tracking system may be advantageous depending on the type of surgical system used such as the one described in U.S. Pat. No. 6,322,567 assigned to the assignee of the present application and incorporated by reference in its entirety.

Surgical Planning and Execution for a Total Knee Arthroplasty (TKA) Application

The surgical plan is created, either pre-operatively or intra-operatively, by a user using planning software. The planning software may be used to a generate three-dimensional (3-D) models of the subject's bony anatomy from a computed tomography (CT), magnetic resonance imaging (MRI), x-ray, or ultrasound image data set. Alternatively, the surgical plan is created using data collected directly from the patient intraoperatively (e.g. digitized points, kinematic femoral head center, ankle center, statistical bone morphing) such as with typical imageless navigation systems rather than using a per-operative image data set. A set of 3-D computer aided design (CAD) models of the manufacturer's prosthesis are pre-loaded in the software that allows the user to place the components of a desired prosthesis to the 3-D model of the boney anatomy to designate the best fit, position and orientation of the implant to the bone.

The surgical plan contains the 3-D model of the patient's operative bone combined with the location of one or more virtual pin planes. The location of the virtual pin plane(s) is defined by the planning software using the POSE of one or more planned cut planes and one or more dimensions of a cutting guide.

Intra-operatively, the surgical plan is registered to the bone. The surgical device 102 then articulates the pin in one-or-more degrees of freedom to align the pin P with a virtual pin plane. Once aligned, the user may command the device 102, via a trigger, to drive (e.g., rotate) the pin P, while manually advancing the pin P into the bone coincident with the virtual pin plane. In some embodiments, the pin P is automatically advanced into the bone with components associated with the surgical device 102. The pin P is inserted into the bone to a degree of bone retention that overcomes the attraction of the pin P to the magnet 56. Therefore, the surgical device 102 may be easily removed from the pin P to assemble and install subsequent pins. Cutting guides are then assembled to the pins to facilitate the creation of the planar cuts that receive the knee prosthesis.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A surgical device for pin insertion in a bone of a subject to aid in performing a bone cutting procedure, the surgical device comprising:
a drive portion configured to drive a threaded pin for insertion into the bone;
a pin drive subassembly of the drive portion with a shaft having a shaft end, at least one magnet associated with the shaft end and exerting an attractive force on the pin placed in the shaft end; and
a spindle subassembly of the drive portion to drive the shaft so as to rotate the pin into the bone to a degree of bone retention that overcomes the attractive force on the pin exerted by the at least one magnet.

2. The device of claim 1 further comprising:
a hand-held portion;
a plurality of fiducial markers attached to or integrated with the drive portion to permit a tracking system to track a position and orientation (POSE) of the drive portion; and
wherein a position and orientation (POSE) of the pin in the bone is used to assemble and align a cutting guide thereon to facilitate the creation of a desired cut plane.

3. The device of claim 1 wherein the shaft further comprises a hex socket that houses the at least one magnet on the shaft end, the shaft configured to accept a male hex end of the pin.

4. The device of claim 1 wherein the at least one magnet is adhesively attached to the shaft.

5. The device of claim 1 wherein the pin drive subassembly further comprises a pin guide having an inner diameter, the inner diameter being tightly dimensioned to an outer diameter of the pin, and fits over the pin with a clearance that constrains a pin rotational axis of the pin to a shaft rotational axis of the shaft.

6. The device of claim 1 wherein the spindle subassembly further comprises:
a bearing cap, a bearing holder, a set of disk springs, a coupler, a motor holder, a motor, and a spindle cartridge, the spindle cartridge having two parallel flange walls and the bearing holder being mechanically connected to a first of the two parallel flange walls and inserted through the spindle cartridge, and the motor holder is mechanically connected to a second opposing flange wall of the two parallel flange walls to facilitate a corridor between the motor and the pin driver subassembly.

7. The device of claim 6 wherein the spindle subassembly further comprises a coupler, wherein the coupler joins an opposing end of the shaft to the motor.

8. An alignment system for surgical bone cutting procedures, comprising:
the surgical device of claim 1;
a tracking system to track a position and orientation (POSE) of the drive portion of the surgical device;
a computing system programmed and operating software to:
define a virtual plane relative to a cut plane to be created on the subject's bone;
determine a relationship between a location of the drive portion of the surgical device and the virtual plane; and
supply a series of commands to the surgical device to control pitch and translation to maintain a pin insertion axis with the virtual plane;
a cutting guide configured to be received on to a plurality of bone pins inserted in a subject's bone with the surgical device; and
one or more guide slots within the cutting guide, the one or more guide slots configured to guide a surgical saw to make surgical cuts on the subject's bone.

9. The alignment system of claim 8 wherein the cutting guide is made of a rigid or semi-rigid material.

10. The alignment system of claim 8 wherein the cutting guide is made of stainless steel, aluminum, titanium, polyetheretherketone (PEEK), polyphenylsulfone, or acrylonitrile butadiene styrene (ABS).

11. The alignment system of claim 8 wherein the surgical bone cutting procedures are used in a total knee arthroplasty or a revision knee arthroplasty.

12. The alignment system of claim 8 wherein the surgical bone cutting procedures are used in high tibial osteotomies, spinal reconstruction surgery, and other procedures requiring precise placement of the cutting guide to aid a surgeon in creating a series of bone cuts.

13. A method for aligning a cutting guide on a subject's bone, said method comprising:
determining one or more cut planes based on a surgical plan obtained with planning software;
determining one or more virtual planes relative to each of the one or more cut planes to be created on the subject's bone;
using the surgical device of claim 1 for aligning and inserting a plurality of threaded bone pins coincident with a virtual plane from the one or more virtual planes; and
attaching a cutting guide configured to clamp on to the plurality of inserted bone pins; the cutting guide having one or more guide slots configured to guide a surgical saw to make surgical cuts on the subject's bone that correspond to the one or more cut planes.

14. The method of claim 13 wherein a location of the one or more virtual planes is defined by the planning software using a position and orientation (POSE) of one or more planned cut planes and one or more dimensions of the cutting guide.

15. The system of claim 1 wherein the pin is a metallic pin.

* * * * *